United States Patent [19]

Vaughan et al.

[11] Patent Number: 4,559,950
[45] Date of Patent: Dec. 24, 1985

[54] DISPOSABLE BIOMEDICAL AND DIAGNOSTIC ELECTRODE

[75] Inventors: Raymond C. Vaughan, Hamburg; David M. DiSabito, Clarence; Norbert J. Mruk, Williamsville; Arthur R. Eddy, Jr., Depew, all of N.Y.

[73] Assignee: Graphic Controls Corporation, Buffalo, N.Y.

[21] Appl. No.: 555,071

[22] Filed: Nov. 25, 1983

[51] Int. Cl.⁴ ............................................. A61B 5/04
[52] U.S. Cl. ................................... 128/641; 128/803
[58] Field of Search ............... 128/639, 640, 641, 644, 128/795, 796, 798, 799, 802, 803; 252/500; 29/877, 857; 106/208

[56] References Cited

U.S. PATENT DOCUMENTS

| | | | |
|---|---|---|---|
| 3,977,392 | 8/1976 | Manley | 128/641 |
| 3,993,049 | 11/1976 | Kater | 128/798 |
| 4,079,731 | 3/1978 | Danby | 128/641 |
| 4,098,945 | 7/1978 | Oehmke | 252/500 |
| 4,237,886 | 12/1980 | Sukurada et al. | 128/303.13 |
| 4,270,543 | 6/1981 | Tabuchi et al. | 128/639 |
| 4,274,420 | 6/1981 | Hymes | 128/798 |
| 4,318,746 | 3/1982 | Claffey et al. | 106/208 |
| 4,367,745 | 1/1983 | Welage | 128/303.13 |
| 4,393,584 | 7/1983 | Bare et al. | 29/877 |
| 4,419,091 | 12/1983 | Behl et al. | 128/803 |

Primary Examiner—Lee S. Cohen
Assistant Examiner—Carol J. Graczyk
Attorney, Agent, or Firm—Michael G. Berkman

[57] ABSTRACT

A disposable biomedical and diagnostic electrode characterized in that functional electrical contact is effected between the skin and an electrically conductive element of the electrode by means of a conductive adhesive, and in that conductive skin contact is enhanced, when necessary, by selective application of a conductive gel contained in and releasable from a storage cavity in the electrode itself. The pressure-released gel establishes a fluid film interface between the patient's skin and the conductive adhesive and, concurrently, provides a highly conductive path between the electrode itself, and the patient's skin.

19 Claims, 5 Drawing Figures

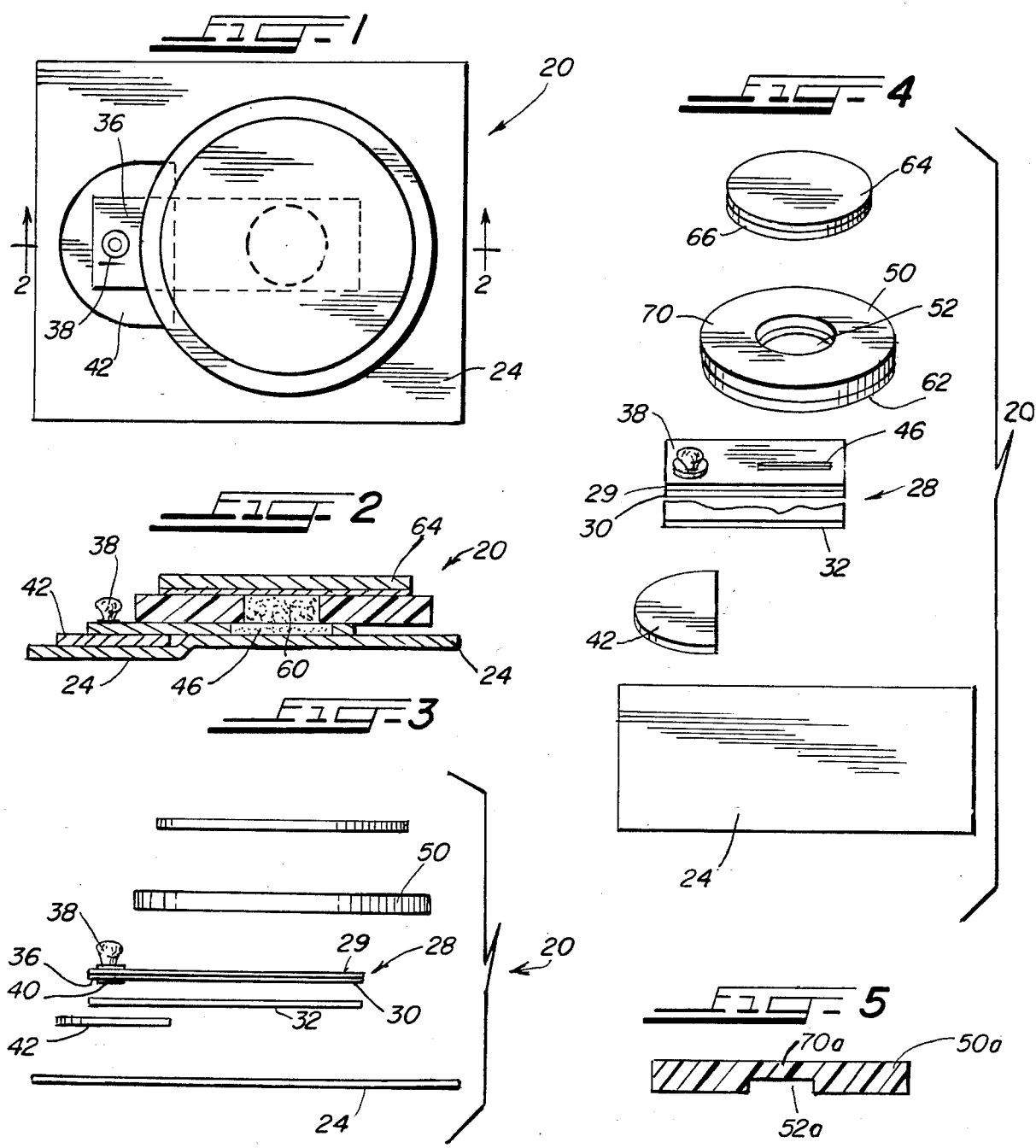

DISPOSABLE BIOMEDICAL AND DIAGNOSTIC ELECTRODE

BACKGROUND OF THE INVENTION

This invention relates to single-use, disposable biomedical and diagnostic electrodes of the type used to detect biological or physiological electrical potentials. Such potentials have long been recognized as being derived from or associated with muscular activity. The electrode of the subject invention is characterized by improved electrical contact with the skin to which it is applied, thereby to establish and maintain a desirable low impedance value and to minimize motion artifacts or electrical noise, without the need for gels, except in special cases.

Many of the electrodes in common use utilize adhesives as means for bonding and securing the electrode in place. For the most part, ECG electrodes of the disposable type are pregelled, the gel itself being contained in a cavity which is often filled with a porous, gel-retaining sponge-like element. While many improvements have been made in various facets of disposable electrodes in recent years, the products available still harbor objectionable features and fall short of fully satisfying the demanding technical requirements and the need for consistently reliable performance. It is, therefore, a principal aim of the present invention to provide an improved disposable electrode which obviates many of the shortcomings of the prior art devices and provides an improved single-use electrode which is of low cost in production so as to be conveniently and economically disposable and which, at the same time, satisfies the demanding standards of function and reliability.

SUMMARY OF THE INVENTION

The present invention relates to a biomedical electrode with improved means for effective electric contact between the electrode and a body surface ensuring high fidelity signal transduction, negligible electrical drift, a minimization of polarization and distortion, and an avoidance of artifacts or noise in the recordings or records produced during use of the electrode. The electrode is particularly suitable for detecting and monitoring low-level electrical signals, the reliability being enhanced by an improved mode of securement of the electrode in place, and by improved electrical contact effected between the electrode itself and the skin surface.

It is an important feature of the electrode of the invention that functional electrical contact is effected between the skin and an electrically conductive element of the electrode by means of a conductive, skin-contacting adhesive.

An additional important feature of the improved electrode structure of the invention is that conductive skin contact is selectively enhanced, when necessary, by application of a conductive gel, the latter being contained in and releasable from a storage cavity in the electrode itself.

A related feature of the electrode of the invention is that there is provided a pressure releasable gel which establishes a fluid film interface bridging between the patient's skin and the conductive adhesive and, concurrently, provides a highly conductive path between the electrode lead line and the patient's skin.

An additional important feature of the electrode is that the gel serves as a stabilizing factor for the adhesive by serving as a humidifier for the adhesive.

A general feature of the invention is that the electrode functions without a gel. Yet a gel is available, at hand, for use in enhancing electrical contact with the patient's skin when such enhancement is found necessary.

It is an important feature of the present invention that the electrode is formed to define a storage cavity constituting a reservoir for a gel composition. A selectably actuable port communicating between the gel reservoir and the patient's skin is defined by a pre-cut slit in the skin-presented support band of the electrode.

A related feature of the invention is that the pre-cut slit in the support band defines an orifice which is in a normally closed or standby mode. The support band is responsive to fluid pressure applied thereagainst to open the slit and to promote gel flow or passage therethrough, from the reservoir cavity, thereby to provide an enhanced electrically conductive path between the conductor lead line of the electrode and an electrode-delineated body zone to which the electrode is adhered.

It is yet another feature of the electrode of the invention that the application of finger pressure to the electrode downwardly thereupon is transmitted to gel in the reservoir cavity and thus impressed against the slit-carrying support band to open the slit and to cause gel to flow therethrough.

It is a feature of the invention that the conductivity of the conductive adhesive is enhanced through the incorporation of electrically conductive particles distributed throughout the adhesive composition.

A principal feature of a preferred embodiment of the electrode of the invention is the use of a conductive adhesive which, in a preferred embodiment of the invention, includes salts dispersed therethrough for rendering the adhesive ionically conductive.

A related feature of the conductive adhesive of the invention is that conductive particles contained therein and distributed therethrough constitute carbon particles.

In still another preferred embodiment of the conductive adhesive of the invention the conductivity properties are enhanced through the incorporation of metallic particles, and in an alternative embodiment, electrical conductivity of the conductive adhesive is enhanced through the incorporation of conductively coated glass spheres or other inert particles.

It is a feature of the electrode of the invention that it may be used, selectively, with and without the release of conductive gel from the storage reservoir.

It is an important practical and utilitarian feature of the improved electrode of the invention that the optional release and use of the conductive gel is effected at the time the electrode is adhesively bonded to the skin surface.

Other and further objects, features, and advantages of the invention will be evident from a reading of the following specification taken in conjunction with the drawings.

BRIEF DESCRIPTION OF THE DRAWINGS

FIG. 1 is a top plan view of an electrode according to the invention, incorporating the features thereof;

FIG. 2 is a cross sectional view taken substantially on the lines 2—2 of FIG. 1;

FIG. 3 is an expanded view showing the relative arrangement of the various stacked components of the electrode of the invention;

FIG. 4 is an exploded perspective showing the component elements of the electrode of the invention; and FIG. 5 is a cross-sectional view of an alternative form of an element of the electrode structure of the invention.

DESCRIPTION OF PREFERRED EMBODIMENT

The aims and objects of the invention are achieved by providing in a disposable biomedical and diagnostic electrode conductive adhesive electrical contact and an optionally usable gel reservoir. Electrical connection and continuity are achieved by means of a conductive adhesive which constitutes a bonding interface interposed between an undersurface of the electrode and the body zone to which the electrode is applied in use. The conductive adhesive is in electrically conductive contact with a conductive element of the electrode to which a lead line may be attached. The electrode of the invention is further characterized in that there is provided a conductive gel reservoir, and in that a selectively actuable port defines passage means communicating between the gel storage reservoir or cavity and the conductive adhesive surface and the skin zone to which the electrode is adhered. At the direction of the user, finger pressure selectively transmitted to the gel contained in the reservoir forces the gel through the port and establishes a film interface between the patient's skin and the conductive adhesive and, concurrently, provides an enhanced conductive path between the electrode itself and the patient's skin.

Referring now to the drawings, there is shown one preferred embodiment of the electrode 20 of the invention provided for illustrative purposes and not to be construed in any limiting sense. The single-use disposable electrode consists of a multi-layer, mult-component structure supported on a peelable release liner 24. The release liner 24 may be a silicone-treated sheet of paper, a plastic film, or other type of release liner as known in the art. A conductive strip 28 with a conductive adhesive 32 applied to its under surface is releasably adhered to the release liner 24. The conductive strip 28 may be a strip of metal or of other selectable conductive materials. In the preferred embodiment of the invention, however, the conductive strip 28 comprises a conductive chemical composition 30 applied to a flexible plastic support band or ribbon 29, as shown in FIG. 3. The support band 29 may be a sheet of MYLAR polyester, for example, while the conductive chemical composition 30 may be a metallic ink such as a silver ink. If desired, the surface of the conductive chemical composition 30 may be chloridized as known in the art in order to improve the electrochemical reversibility of the electrode 20.

At the end portion 36 of the conductive strip 28, projecting laterally beyond the principal body structure of the electrode itself, there is attached a snap fastener stud 38 and eyelet 40 for the convenient snap-on attachment of a lead line (not shown) during electrode use. A lead line may be secured through other expedients, for example, by attachment of a clamping clip to the projecting end portion 36 of the strip 28. In contemplation of the latter option, a tab 42 of plastic or similar nonconductive material is secured on the undersurface of the strip 28 to project beyond the end of the strip 28 and to serve as an insulating shield between the electrical clip (not shown) and the patient's body.

The electrically conductive strip 28 is provided with a die-cut slit 46 which in an undisturbed state is essentially "closed". The slit 46, illustrated schematically, is best seen in the exploded perspective of FIG. 4. Holes may be substituted for the slit.

Superimposed on and bonded to and overlying the strip 28 is a cushion-like wafer or washer-like disk 50 of a relatively soft and compressible, inert foamed plastic. The disk 50 is formed with a circular cut-out area 52 and, in the positioning of the disk 50 with respect to the strip 28, an in-line axial registration is established between the cut-out area 52 of the disk 50 and the slit 46 in the strip 28 therebelow (FIG. 2). It will be appreciated that in the structure described, there is provided a cavity which is defined by the cut-out 52 in the disk 50 and which is closed at its base by the strip 28.

In accordance with the practice of the invention, the open-top cavity is filled with a conductive gel 60. Many suitable conductive gel compositions are known in the art, and the specific composition of the gel itself is not critical in the practice of the present invention.

However, in preferred embodiments of the invention, the gel should contain a substantial concentration of a humectant, for example, at least about 50% by weight of glycerol.

It should be understood that the underface of the disk to is coated with an adhesive composition 62 so that, in assembly, the disk 50 is secured not only to the strip 28 but also to the peelable release liner 24 therebelow and extending laterally thereabout.

In the specific embodiment of the electrode illustrated, the open top of the cavity 52 is closed or sealed by means of a plastic cover 64 which is coated on its underside with an adhesive 66, so that the closure 64 is securely bonded and sealed to the top surface 70 of the foam washer 50. In its fully assembled form, the electrode 20 assumes the structure illustrated schematically in FIG. 2.

While the above detailed description is directed to one preferred embodiment of the invention, it will be understood that variations involving both structure and composition may be made without departing from the invention itself. For example, it is within the contemplation of the invention that the need for a surmounting cavity seal or special closure 64 may be obviated by adopting a variation in the physical configuration of the cavity-defining pad. As shown (FIG. 5), the foam disk 50a is not cut through in the cavity-defining zone 52a. Rather, a residual surmounting portion 70a of the foam disk 50a defines a top "closure" for the cavity 52a.

It is believed that the method of use of the electrode of the invention will be apparent from the foregoing detailed description. Specifically, the electrode is applied to the selected skin surface zone by a conventional procedure. First, one removes the peelable release liner 24 to expose the adhesive-coated surfaces of the conductive strip 28 and of the foam disk 50. Electrical contact between the skin surface and the conductive strip 28 is established through the conductive adhesive 32, and the electrical circuit between the skin and the snap fastener terminal 38 or the end zone 36 of the strip 28 itself is completed. Should it be deemed necessary or expedient to provide an enhanced electrically conductive path between the conductive strip 28 and the body surface, one need merely press downwardly on the foam pad 50 which houses the reservoir 52 for the conductive gel 60. Pressure so applied to the electrode causes the stored gel 60 to transfer pressure against the strip 28 in that region of the strip which is formed with the slit 46. The applied pressure causes the slit 46 to open and permits the flow of conductive gel 60 therethrough. It is presently contemplated that in the majority of cases, the electrical contact effected through reliance solely on the conductive adhesive 32 will be adequate to ensure the requisite circuit integrity and continuity. Only in a relatively small percentage of uses, for example, where the patient's skin is covered with a substantial concentration of hair fibers will the utilization of the gel be dictated.

In the embodiments of the invention in which the band 28 is a plastic film segment, it is contemplated that the conductive surface may be established by applying a metal-containing ink formulation. It is to be understood that various formulations of conductive adhesives may be used in the practice of the present invention. None of these formulations constitutes, per se, an element of the present invention. In the preferred embodiment of the present invention, however, the principal mode of electrical transmission through the conductive adhesive will be by ions rather than by electrons, and the thickness of the conductive adhesive layer 32 will be small, preferably less than 10 mils. Ionic conductivity provides superior electrochemical reversibility and hence superior signal transmission fidelity in a biomedical electrode, while thinness of the conductive adhesive layer allows the conductive adhesive layer to conform to the skin, thus maintaining uniform electrical properties.

It is contemplated that the conductivity of such adhesives may be enhanced through the incorporation of fillers including salts or electrically conductive particles. Such particles may be metallic particles, or, alternatively, carbon particles, or other inert particles, or glass coated with suitable conductive materials. While preferred embodiments of the invention have been illustrated, other variations may be made utilizing the inventive concepts herein disclosed. It is intended that all such variations in functional structures and in compositions be considered as within the scope of the invention as defined in the following claims.

What is claimed is:

1. A disposable electrode for medical diagnostic and biomedical use, and for clinical use,
    said electrode comprising a composite assembly including:
    a support sheet connected to and surmounting said assembly,
    said support sheet comprising a wafer-like disk having an underside for application of an adhesive thereon,
    said disk being formed with a gel storage cavity defining reservoir means for confining a conductive gel therein,
    a conductive gel stored in said reservoir means,
    band means bridging said gel storage cavity and serving as a bottom closure for said reservoir means,
    said band means having an upper surface presented to said support sheet and a lower surface for securement to a patient's body,
    adhesive means bonding said upper surface of said band means to said support sheet on said underside thereof,
    a conductive adhesive composition constituting a conductive layer coating said lower surface of said band means for adhesively securing said electrode to a patient's body,
    said band means including means in electrically conductive communication with said conductive adhesive composition for attachment of an electrical lead line thereto,
    port means including passage-defining means formed in said band means for providing fluid-flow communication between said reservoir means and said conductive adhesive composition for releasing said gel from said reservoir means,
    said port means being normally constricted and being selectively actuable to open to release gel from said reservoir means and to provide an enhanced conductive path between said conductive adhesive composition and a body surface to which said electrode is applied.

2. The structure as set forth in claim 1 wherein said support sheet comprises a foamed, soft, plastic disk.

3. The structure as set forth in claim 1 wherein said port means includes pre-cut slit means in said band means for permitting flow of said gel from said reservoir means.

4. The structure as set forth in claim 3 wherein said slit means is in a normally-closed, stand-by mode, and wherein said band means is responsive to fluid pressure applied thereagainst to open said slit means and to promote gel flow therethrough from said reservoir means and to provide an enhanced electrically conductive path between said conductive adhesive composition and an electrode-delineated body zone to which said electrode is adhered.

5. The structure as set forth in claim 1 wherein said reservoir means comprises a vertically extending transverse through passage in said support sheet, and further comprising a cover surmounting said passage and bonded to a top surface of said support sheet as a top closure for said reservoir means.

6. The structure as set forth in claim 1 further comprising means for applying finger pressure to said electrode to transfer said gel in said reservoir means and against said port means to open said port means and to cause gel to flow therethrough from said reservoir means.

7. The structure as set forth in claim 1 wherein said band means includes an end portion extension for connecting an electrical lead line to said band means.

8. The structure as set forth in claim 7 and further comprising tab-like insulator means and means securing said insulator means to said electrode on said lower surface of said band means for insulating electrically between said end portion extension of said band means and the body of a wearer of said electrode.

9. The structure as set forth in claim 1 wherein said band means consists essentially of a plastic film segment, and further comprising a conductive coating applied to said plastic film segment as an interface between said film segment and said conductive adhesive composition.

10. The structure as set forth in claim 1 wherein said conductive adhesive composition includes salt means dispersed therethrough for rendering said conductive adhesive composition ionically conductive.

11. The structure as set forth in claim 1 and further comprising filler means including electrically conductive particles distributed throughout said conductive adhesive composition for enhancement of electrical conductive properties thereof.

12. The structure as set forth in claim 1 wherein said means in electrically conductive communication with said conductive adhesive composition includes a snap fastener element.

13. The structure as set forth in claim 11 wherein said electrically conductive particles include metallic particles.

14. The structure as set forth in claim 11 wherein said electrically conductive particles include carbon particles.

15. The structure as set forth in claim 11 wherein said electrically conductive particles include coated glass spheres.

16. The structure as set forth in claim 1 wherein said conductive adhesive composition has a through thickness not exceeding 10 mils.

17. The structure as set forth in claim 9 wherein said conductive coating comprises a silver ink and wherein said conductive coating is chloridized.

18. The structure as set forth in claim 1 wherein said conductive gel contains a humectant, and wherein the concentration of humectant in said conductive gel is at least about 50% by weight.

19. The structure as set forth in claim 1 wherein said band means consists essentially of an electrically conductive metallic strip.

* * * * *